United States Patent
Gaudillière

(10) Patent No.: US 6,787,554 B2
(45) Date of Patent: Sep. 7, 2004

(54) TRIAZOLO[4,3-A]PYRIDO[2,3-D]PYRIMIDIN-5-ONE DERIVATIVES

(75) Inventor: Bernard Gaudillière, Nanterre (FR)

(73) Assignee: Warner-Lambert LLC, Morris Plains, NJ (US)

( * ) Notice: Subject to any disclaimer, the term of this patent is extended or adjusted under 35 U.S.C. 154(b) by 0 days.

(21) Appl. No.: 10/303,103

(22) Filed: Nov. 22, 2002

(65) Prior Publication Data

US 2003/0187257 A1 Oct. 2, 2003

(30) Foreign Application Priority Data

Nov. 26, 2001 (FR) ............................................ 01 15249

(51) Int. Cl.⁷ ..................... A61K 31/519; C07D 471/14
(52) U.S. Cl. .................. 514/267; 514/217.06; 540/600; 544/251
(58) Field of Search ........................... 514/267, 217.06; 544/251; 540/600

(56) References Cited

FOREIGN PATENT DOCUMENTS

| DE | 3601731 | 7/1987 | ......... C07D/471/04 |
|----|---------|--------|------------------------|
| EP | 0076199 | 12/1986 | ......... C07D/487/04 |
| EP | 0316668 | 5/1993 | ......... A61K/31/505 |
| EP | 0243311 | 6/1993 | ......... C07D/471/04 |
| EP | 0994113 | 4/2000 | ......... C07D/471/04 |
| EP | 1145716 | 10/2001 | ......... A61K/31/519 |
| WO | 9208719 | 5/1992 | ......... C07D/471/04 |
| WO | 0066584 | 11/2000 | ......... C07D/487/04 |

OTHER PUBLICATIONS

Beavo J A et al, 1990, Trends Pharmacol. Sci, 11, 150–155.
Beavo J A et al, 1994, Molecular Pharmacol, 46, 399–405.
Ram et al., J. Prakt. Chem., 1990, 332(5), 629–39.
J. Het. chem, 1982, 19, 1461.
Berge S. M. et al, J. Pharm. Sci, 1997, 66, 1–19.
Journal of Pharm Sci., 1996, 85(11), 1142–69.
T.J. Torphy et al., J. Pharm. Exp. Ther., 1992, 263, 1195–205.
Lavan B. E. et al., Biochemical Pharm., 1989, 38(22), 4123–36.
Silver P. J. et al., Eur. J. Pharmacol, 1988, 150, 85–94.
Luckow V. A. et al., Recomb. DNA Technol. & Appl. Eds. Prokop, Bajpa R. K. & Ho C. S., 1991, 97–152.
Advances in Cyclic Nucleotide research, Ed. G. Brooker et al., Raven Press, NY, 1979, 10, 69–92.

*Primary Examiner*—Richard L. Raymond
(74) *Attorney, Agent, or Firm*—Peter C. Richardson; Gregg C. Benson; Robert T. Ronau

(57) ABSTRACT

The invention relates to triazolo[4,3-a]pyrido[2,3-d] pyrimidine-5-one derivatives, their regioisomers, their salts and their solvates if they exist, their preparation, compositions containing them and their use. These derivatives possess properties inhibiting PDE4 and/or the release of TNFα, and may therefore be used for the treatment or prevention of numerous conditions by virtue of the inhibition of the PDE4 enzyme and the resulting increase in the cAMP level.

18 Claims, No Drawings

TRIAZOLO[4,3-A]PYRIDO[2,3-D]PYRIMIDIN-5-ONE DERIVATIVES

The present invention relates to triazolo[4,3-a]pyrido[2,3-d]pyrimidine-5-one derivatives of general formula (I):

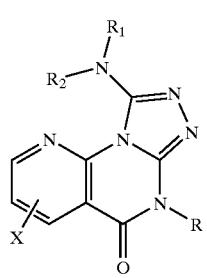

(I)

in which R1, R2, X and R have the meanings indicated below, their regioisomers, their salts and their solvates if they exist, their preparation, compositions containing them and their use.

Cyclic adenosine 3',5'-monophosphate (cAMP) is an omnipresent second intracellular messenger. More recently, cAMP is an intermediate between the first messenger (hormone, neurotransmitter or autacoid) and functional cell responses. The first messenger stimulates the enzyme responsible for the synthesis of cAMP which then becomes involved, depending on the relevant cells, in a large number of functions (metabolic, contractile or secretory functions for example). The effects of cAMP stop when it is degraded by cyclic nucleotide phosphodiesterases (PDE), which are intracellular enzymes which catalyse the hydrolysis of cAMPs to inactive adenosine 5'-monophosphate.

At least 11 large families of phosphodiesterases (PDE) have been identified in mammals. These families are numbered from 1 to 11 according to their structure, their kinetic behaviour, their substrate specificity or their sensitivity to effectors (Beavo J. A. et al., 1990, Trends Pharmacol. Sci., 11, 150–5; Beavo J. A. et al., 1994, Molecular Pharmacol., 46, 399–405).

Nonspecific PDE inhibiting compounds, that is to say which inhibit several families of enzymes, are known. That is the case, for example, for certain methylated xanthines such as theophylline. These compounds have a low therapeutic index, in particular because of their action on types of PDE present in cells other than the target cells. Conversely, some families of PDE may be selectively inhibited by various pharmacological agents. The hydrolysis of cyclic nucleotides is then slowed and their concentration increases as a result, but only in the cells containing the type of PDE sensitive to the inhibition.

One particular advantage of the PDE4 enzymes has been shown. Indeed, these enzymes are widely represented in the inflammatory and immunocompetent cells, and induce a reduction in the level of cAMP. The inhibition of these enzymes by PDE4-specific inhibitors thus leads to an intracellular increase in cAMP and to a consequent decrease in the functions of the inflammatory cells. In addition, cAMP reduces the tonicity of the smooth muscle fibres of the airways. Thus, PDE4 inhibitors also cause bronchorelaxation. Various experiments in models of pulmonary inflammation such as that described in asthma have, for example, shown that PDE4 inhibitors induce a drastic reduction in the influx of the inflammatory cells and a considerable decrease in bronchial hyperreactivity. Recently, the use of PDE4 inhibitors has also been recommended in the treatment of chronic obstructive pulmonary disease and rheumatoid arthritis. Moreover, as PDE4 inhibitors have been described as potential blockers of the production of TNFα, these compounds ought to be beneficial in the context of the treatment of a pathology involving this proinflammatory cytokine.

Thus, numerous research studies have been carried out in order to identify selective PDE4 inhibitors having a therapeutic activity as anti-inflammatory and anti-allergic medicaments, and in the treatment of various respiratory diseases such as asthma, emphysema and chronic bronchitis. These research studies are long and difficult since a number of potential PDE4 inhibitors are not free of activity on the phosphodiesterases of the other families. To date, the lack of selectivity of the PDE4 inhibitors therefore represents a major problem, given the large number of functions regulated by cAMP. Adding to this problem is the fact that the PDE4 inhibitors proposed up until now quite often induce undesirable effects, in particular nausea and vomiting. In parallel, the PDE4 inhibitors proposed up until now sometimes exhibit poor overall bioavailability.

Patent application WO 00/66584 proposes selective PDE4 inhibitors of formula:

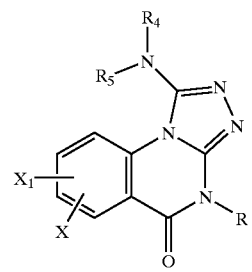

Other publications also describe triazoloquinazolinone derivatives having a structural unit similar to the structure indicated above and which carry various substituents, for the treatment of asthma, bronchitis and allergic disorders (EP 0 076 199), as diuretic and antianaphylactic agents (DDR 158 549), or as antihypertensives (Ram et al., J. Prakt. Chem., 1990, 332 (5), 629–39).

Application WO 92/08719 describes compounds of formula:

which are useful as herbicides.

On the basis of the same structural unit, but carrying other substituents, there have finally been described:
1) the compounds of formula:

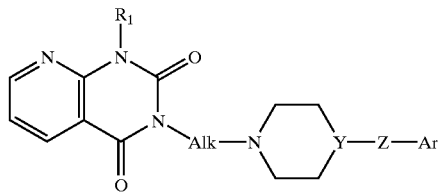

as antihypertensives (DE 3601731) or as analgesics (EP 0 316 668),
2) the compounds of formula:

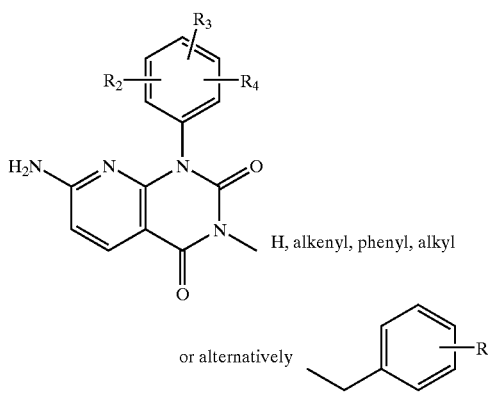

for treating bronchial asthma (EP 0 994 113) or for treating dermatitis when the substituent is a benzyl (EP 1 145 716),
3) the compounds of formula:

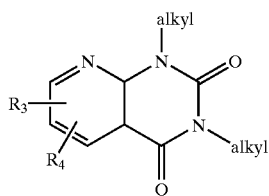

as antiallergics (EP 0 243 311).

It has now been found that the triazolo[4,3-a]pyrido[2,3-d]pyrimidin-5-one derivatives of general formula (I) in which:
X represents a radical chosen from:
  hydrogen,
  hydroxyl, halogen, amino, nitro, mercapto, cyano or carboxyl radicals,
  alkyl, alkoxy, alkylthio, alkylsulphinyl or alkylsulphonyl radicals optionally substituted with 1, 2 or 3 halogen atoms,
  the radicals —NR3R4 with R3 and R4, which are identical or different, chosen from the following radicals:
    hydrogen,
    alkyl optionally substituted with 1, 2 or 3 groups chosen from halogen, hydroxyl, cyano and alkoxy,
    —C(O)R5 with R5 chosen from hydrogen or alkyls optionally substituted with a hydroxyl, alkoxy, mercapto or alkylthio radical,
    —(CH2)x-cycloalkyl optionally substituted with a hydroxyl, alkoxy, mercapto, alkylthio, amino, alkylamino, N-alkyl, N-alkylamino or alkyl radical comprising 1, 2, 3 or 4 carbon atoms in the form of a linear or branched chain, x being an integer chosen from 0, 1, 2, 3 and 4,
the radicals of formula:

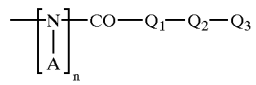

in which:
  n is an integer chosen from 0 and 1,
  when n=1, then A represents either a hydrogen atom or a substituent CO—Q1—Q2—Q3,
  Q1 represents a radical oxy(—O—), —NH—,

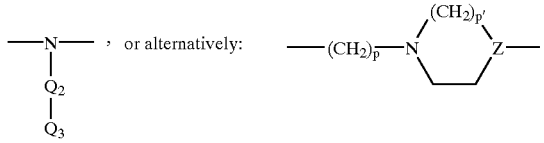

p and p' being integers chosen, independently of each other, from 0, 1, 2 and 3 and Z representing a —CH—, —N— or alternatively oxy group,
  Q2 represents either a group —(CH2)q—, q being an integer chosen from 0, 1, 2, 3 and 4, or a group —(CH2—CH2—O)r—, r being an integer chosen from 2, 3 and 4, and
  Q3 represents a hydrogen atom or a radical chosen from hydroxyl, methoxy, —O—CO—X1, —NHX2 and —N(X1)X2, X1 and X2, which are identical or different, representing an alkyl radical or X1 and X2 being linked such that they form, together with the nitrogen atom to which they are attached, an azacycloalkyl radical comprising 3, 4, 5, 6, 7, 8, 9 or 10 members and being capable, in addition, of comprising 1, 2 or 3 heteroatoms chosen from oxygen, sulphur and/or nitrogen,
it being possible for the substituents —CO—Q1—Q2—Q3 to be identical or different within the same unit of formula [N(A)]n—CO—Q1—Q2—Q3, and
the radicals of formula:

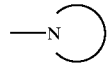

in which the ring formed with the nitrogen atom comprises 3, 4, 5, 6, 7, 8, 9 or 10 members and may, in addition, comprise 1, 2 or 3 heteroatoms chosen from oxygen, sulphur and/or nitrogen, it being possible for the said ring to also be bridged by an alkyl, to be gem dialkylated or substituted with 1, 2 or 3 groups chosen from hydroxyl, oxo, alkyl and/or alkoxy radicals or with a group —CO—Q1—Q2—Q3 as defined above,
R represents a radical chosen from:
  alkyl, alkenyl, alkynyl, 2-, 3- or 4-pyridylalkyl radicals, it being possible for the said pyridyls to be optionally substituted once, twice or three times with alkyl, alkoxy, hydroxyl, halogen and/or amino radicals, the radicals of the following formulae:

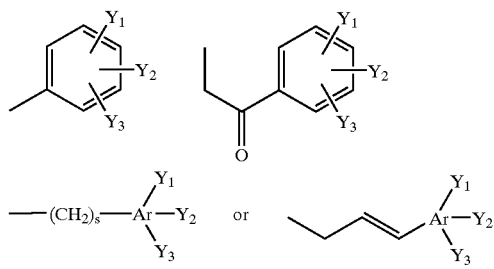

in which:
s is an integer chosen from 1, 2, 3 and 4,
Ar represents a 5- or 6-membered aryl radical which may comprise, in addition, 1, 2, 3 or 4 heteroatoms chosen from oxygen, sulphur and/or nitrogen,
Y1, Y2 and Y3, which are identical or different, are radicals chosen from:
hydrogen, hydroxyl, mercapto, amino, nitro, halogen,
—C(O)R6, —C(O)OR6, —C(O)NR6R7, —NR6R7, —(CH2)t—CN or —(CH2)t—C(O)—Q1—Q2—Q3, t being an integer chosen from 0, 1 and 2, Q1, Q2 and Q3 being as defined above, and R6 and R7, which are identical or different, representing a hydrogen or an alkyl radical or alternatively R6 and R7 being linked such that they form, together with the nitrogen atom to which they are attached, an azacycloalkyl radical comprising 4, 5, 6 or 7 members and which may comprise, in addition, 1, 2 or 3 heteroatoms chosen from nitrogen, oxygen and/or sulphur,
alkyl, alkoxy, alkylthio, alkylsulphinyl or alkylsulphonyl, these radicals being optionally substituted with 1, 2 or 3 halogen atoms,
R1 and R2 represent:
alkyl radicals when R1 and R2 are identical, or alternatively
when R1 and R2 are different, alkyl, aralkyl, cycloalkyl or cycloalkylalkyl radicals,
or alternatively, R1 and R2 are linked such that they form, together with the nitrogen atom to which they are attached, an azacycloalkyl radical comprising 4, 5, 6 or 7 members and which may comprise, in addition, 1, 2 or 3 heteroatoms chosen from oxygen, sulphur and/or nitrogen, it being possible for the said ring thus formed to be optionally bridged by an alkyl, to be gem dialkylated or substituted with 1, 2 or 3 groups chosen from hydroxyl, oxo, alkyl, alkoxy or phenylalkyl radicals and/or a group —CO—Q1—Q2—Q3 as defined above, it being possible for two of the atoms of the said ring thus formed to also form part of another ring chosen from phenyl and heteroaryl having 4, 5, 6, 7 or 8 members and comprising, in addition, 1, 2, 3 or 4 heteroatoms chosen from oxygen, sulphur and/or nitrogen,
and their regioisomers, their salts and their solvates if they exist, are PDE4 enzyme inhibitors which constitute a particularly advantageous alternative to the already known inhibitors because they possess a range of properties (selectivity towards the PDE4 enzyme, pharmacokinetics, toxicity and the like) which are globally favourable for possible industrial development.

For the compounds of general formula (I) according to the present invention, when radicals or substituents appear more than once, they may all have the meanings indicated independently of each other. In particular, they may be identical or different from each other. In the case of combined radicals, the free bond by which the said radical is attached starts from the group indicated at the end of the name of the said radical. For example, in the case of an aralkyl radical, the free bond by which the said aralkyl radical is attached starts from the alkyl group which itself carries an aryl group as substituent, that is:

—alkyl—aryl

According to the present invention, the halogen atoms are generally chosen from fluorine, chlorine, bromine or iodine. Preferably, the halogen atoms according to the present invention are chosen from bromine and chlorine.

In general formula (I) above, the alkyl radicals relate more precisely to the alkyls comprising 1, 2, 3, 4, 5 or 6 carbon atoms in the form of a straight or branched chain, unless otherwise specified. This also applies to the substituted alkyls or to the alkyls as substituents of other radicals, such as for example alkoxy, alkylamino, N-alkyl, N-alkylamino, alkylthio, alkylsulphinyl, alkylsulphonyl, pyridylalkyl, alkoxycarbonyl and aralkyl radicals, and the like. The alkyl radicals according to the present invention may be more precisely chosen from methyl, ethyl, n-propyl, isopropyl, n-butyl, isobutyl, sec-butyl, tert-butyl, n-pentyl, isopentyl, neopentyl, tert-pentyl, 2-methylbutyl, 3-methylbutyl, 1-ethylpropyl, n-hexyl, isohexyl, neohexyl, tert-hexyl, 1-methylpentyl, 2-methylpentyl, 3-methylpentyl, 1,2-dimethylbutyl, 1,3-dimethylbutyl, 2,2-dimethylbutyl, 2,3-dimethylbutyl, 1,2,3-trimethylpropyl, 1,1,2-trimethylpropyl or 1,2,2-trimethylpropyl, 1-ethylbutyl, 2-ethylbutyl, 1-isopropylpropyl and 1-ethyl-1-methylpropyl radicals. Preferably, the alkyl radicals are chosen from methyl, ethyl, n-propryl, isopropyl, n-butyl, isobutyl, sec-butyl, tert-butyl, n-pentyl, isopentyl, n-hexyl and isohexyl. In the case where the alkyl radicals are substituted with halogen atoms, they are preferably fluorine atoms, and the trisubstituted groups of the —(CH2)w—CF3 type are preferred with w an integer between 0 and 3 inclusive. For example, in the case of a methyl, trifluoromethyl is preferred.

The alkenyl and alkynyl radicals also contain 2, 3, 4, 5 or 6 carbon atoms in a straight or branched chain. More preferably, the alkenyl and alkynyl radicals contain 3 or 4 carbon atoms. Suitable alkenyl radicals according to the present invention are for example vinyl, propen-1-yl, allyl, 3-buten-1-yl, 2-methylbuten-1-yl, 2-methylpropen-1-yl, 2-methylpropen-2-yl or 3-methylbuten-2-yl. Suitable alkynyl radicals according to the present invention are, for example, ethynyl, propyn-1-yl, propyn-2-yl, 3-butyn-1-yl, 2-methylbutyn-1-yl or hexynyl.

For the purposes of the present invention, the expression cycloalkyl radical is understood to mean monocyclic saturated hydrocarbons comprising 3 to 10 members. More preferably, the cycloalkyl radicals according to the present invention comprise 3 to 6 members. By way of example, the cycloalkyl radicals may be chosen from cyclopropyl, cyclobutyl, cyclopentyl, cyclohexyl, cycloheptyl, cyclooctyl, cyclononyl and cyclodecyl. These radicals may be optionally, according to certain aspects of the present invention, bridged by an alkyl. The radical then becomes a bicycloalkyl radical. Optionally, these cycloalkyl or bicycloalkyl radicals may, in addition, contain 1 to 3 heteroatoms chosen from nitrogen, oxygen and/or sulphur, which can occupy any place on the ring, whether it is bridged or otherwise. They may also be situated on the bridge or, in the case of the nitrogen atom, constitute a bridge head. The free bond of the cycloalkyl and bicycloalkyl radicals may also occupy any place on the ring. By way of example of bridged cycloalkyls, there may be mentioned the radicals which are derived from norbornane (bicyclo[2.2.1]heptane), bicyclo [2.2.2]octane, bicyclo[3.2.1]octane, bicyclo[1.1.0]butane or bicyclo[5.2.0]nonane. By way of example of cycloalkyl radicals containing one or more heteroatoms, there may be mentioned the radicals which are derived from aziridine, oxirane, 1,2-oxothiolane, piperazine or morpholine. By way of example of bridged cycloalkyls containing one or more heteroatoms, there may be mentioned 7-azabicyclo[2.2.1] heptane, quinuclidine or 2-oxobicyclo[2.2.1]heptane. Finally, according to a final aspect of the present invention, the (bi)cycloalkyl radicals optionally containing one or more heteroatoms may, in addition, contain one or more unsaturations. By way of example of such radicals, there may be mentioned the radicals which are derived from norbornene or bornene.

For the purposes of the present invention, the expression aryl radical is understood to mean univalent monocyclic or polycyclic aromatic hydrocarbon radicals comprising 6 to 14 members, unless otherwise specified. According to a preferred aspect, the aryl radicals of the present invention comprise 5 or 6 members. The free bond may occupy any place on the said aryl radical. By way of example, the phenyl, 1-naphthyl, 2-naphthyl, 2-biphenylyl, 3-biphenylyl, 4-biphenylyl, pentalenyl, indenyl, azulenyl, heptalenyl or anthryl radicals may be mentioned.

According to one variant of the present invention, the aryl radicals may, in addition, comprise 1, 2, 3 or 4 heteroatoms chosen from oxygen, sulphur and/or nitrogen. In this case, the said radicals become so-called heteroaryl radicals. By way of example of heteroaryl, there may be mentioned the radicals which are derived from thiophene, benzo[b] thiophene, furan, isobenzofuran, phenoxanthine, xanthene, pyrrole, imidazole, pyrazole, pyridine, pyrazine, pyrimidine, pyridazine, indolizine, isoindole, indole, purine, isoquinoline, quinoline, phthalazine, 1,8-naphthyridine, quinoxaline, cinnoline, pteridine, phenanthridine, acridine, 1,7-phenanthroline, phenazine, isothiazole, isoxazole, furazan.

According to the invention, the compounds of formula (I) may be prepared by addition of a compound of formula R-Q in which R is as defined for general formula (I) and Q represents, for example, a mesylate, tosylate or triflate radical or alternatively a halogen atom, for example chosen from fluorine, chlorine, bromine or iodine, to a compound of formula (II):

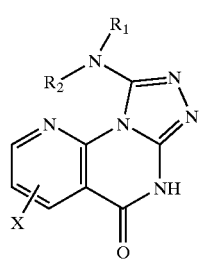
(II)

in which the radicals R1, R2 and X are as defined above in general formula (I).

The reaction is generally carried out in a basic medium, at a temperature of between 20° C. and 150° C., in an appropriate organic solvent. As compatible base, there may be used alkali or alkaline-earth metal carbonates, for example caesium, potassium or sodium carbonate or alternatively sodium hydride. The procedure is preferably carried out in an appropriate solvent chosen from dimethylformamide, dimethyl sulphoxide, N-methylpyrrolidone or 1,2-dimethoxyethane.

The compound of formula R-Q is either a commercially available product, or it can be easily prepared according to the customary organic chemistry techniques well known to persons skilled in the art. To this effect, reference may be made, for example, to the methods described by Jerry March (Advanced Organic Chemistry: Reactions, Mechanisms and Structure, 3rd Edition, Wiley-Interscience Publication, 1985).

The compounds of general formula (II) may be prepared by N-debenzylation of the compounds of formula (III):

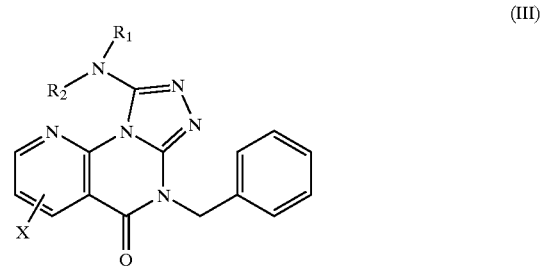
(III)

in which R1, R2 and X are as defined above.

The N-debenzylation reaction is carried out by treatment in the presence of an acidic reagent chosen in particular from Lewis acids, for example aluminium chloride. Preferably, the procedure is carried out at a temperature of between 0° C. and 100° C. and in an appropriate solvent preferably chosen from aromatic solvents such as benzene or toluene.

It should be noted that the compounds of general formula (III) indicated above are intermediates for the preparation of certain compounds of general formula (I) but may also constitute the final compounds according to the present invention as such (in the case where the substituent R is a benzyl radical). In this case, the compounds of general formula (III) may be purified and isolated with no further reaction step.

The compounds of general formula (III) may be obtained by substitution of an amine of formula R1—NH—R2, R1 and R2 being as defined above, onto the corresponding halogenated compound of formula (IV):

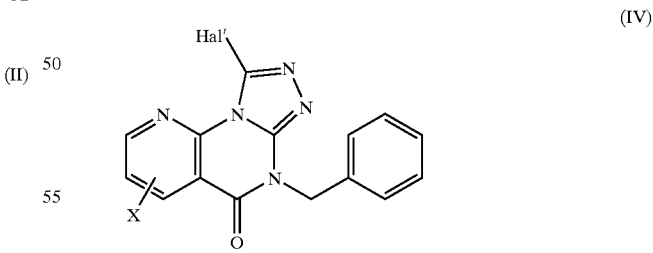
(IV)

in which X is as defined above and Hal' represents a chlorine, bromine or iodine atom.

The action of the amine is generally carried out at a temperature of between 20° C. and 150° C. in the presence of an excess of the amine and optionally in the presence of a base such as, for example, sodium bicarbonate, potassium bicarbonate or potassium carbonate. Preferably, the procedure is carried out in suitable organic solvents, advantageously an aprotic polar solvent such as pyridine, dimethylformamide, dimethyl sulphoxide, N-methylpyrrolidone or acetonitrile. It is also optionally possible to carry out the procedure in the absence of solvent.

The compounds of general formula (IV) may be prepared by chlorination or bromination of the compounds of formula (V):

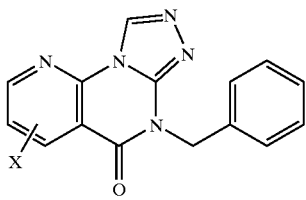

(V)

in which X is as defined above.

The chlorination or bromination reaction is carried out by treatment with chlorine or bromine, in an appropriate organic solvent such as, for example, chloroform and at a temperature generally of between 15° C. and 100° C.

The compounds of formula (V) may be prepared by cyclization of the hydrazino derivatives of formula (VI):

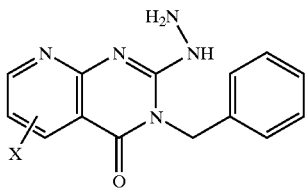

(VI)

in which X is as defined above.

The cyclization reaction is carried out by the action, on the compounds of formula (VI), of alkyl orthoformate (for example a methyl or ethyl orthoformate), in a solvent such as chloroform or benzene, optionally in the presence of an acid such as sulphuric acid or hydrochloric acid. Generally, the procedure is carried out at a temperature of between 0° C. and 100° C.

The compounds of formula (VI) may be prepared from the corresponding thiocarbonyl derivative of formula (VII):

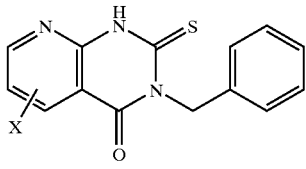

(VII)

in which X is as defined above.

The reaction is generally carried out by treating with hydrazine hydrate in an appropriate solvent such as aqueous-alcoholic solutions (for example methanol or ethanol). Generally, the procedure is carried out at a temperature of between 20° C. and 80° C., and advantageously at the reflux temperature of the mixture.

The thiocarbonyl derivatives of formula (VII) may be prepared by the action of benzyl isothiocyanate on the 2-aminonicotinic acid derivatives of formula (VIII):

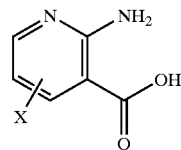

(VIII)

in which X is as defined above.

The treatment with benzyl isothiocyanate is generally carried out at a temperature of between 20° C. and 120° C., and advantageously at the reflux temperature of the mixture, in a suitable solvent such as, for example, pyridine or acetic acid.

When X represents a hydrogen atom, the product of general formula (VIII) is commercially available. If X is not a hydrogen atom, then the product of general formula (VIII) is obtained using customary organic chemistry techniques known to persons skilled in the art. To this effect, reference may be made, for example, to the methods described by Jerry March (Advanced Organic Chemistry: Reactions, Mechanisms and Structure, 3rd Edition, Wiley-Interscience Publication, 1985) or in J. Het. Chem., 1982, 19, 1461.

According to another alternative of the present invention, the compounds of formula (IV) may be prepared by chlorination or bromination of the corresponding methylthio compounds of formula (V'):

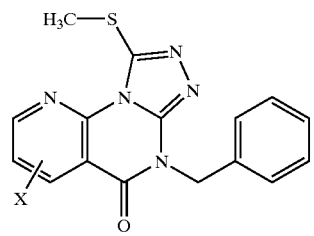

(V')

in which X is as defined above.

The chlorination or bromination reaction is generally carried out by treating with chlorine or bromine in an appropriate solvent, particularly chlorinated solvents and in particular chloroform, and at a temperature generally of between 0° C. and 40° C.

The compounds of formula (V') may be prepared by alkylation of the corresponding mercapto derivatives of general formula (VI'):

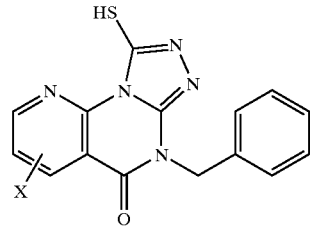

(VI')

in which X is as defined above.

The reaction is generally carried out by treatment with an alkylating, in particular methylating, agent such as, for example, dimethyl sulphate. Advantageously, the procedure is carried out in the presence of an aqueous base such as, for example, aqueous sodium hydroxide and at a temperature generally between 15° C. and 60° C., and preferably at room temperature.

The compounds of formula (VI') may be obtained from the compounds of formula (VI) as described above, by treatment with potassium xanthogenate or according to another alternative by treatment with carbon disulphide. The procedure is generally carried out at a temperature of between 20° C. and 120° C., and advantageously at the reflux temperature of the mixture, in a suitable solvent such as, for example, pyridine or acetic acid.

For certain steps of the overall method of synthesis set out above, it may be necessary to protect the possible reactive functional groups which it is not desired to cause to react. In this case, any protecting group is used which is compatible with the molecule and whose use or removal does not adversely affect the rest of the molecule. In particular, the procedure is carried out according to the methods described by T. W. GREENE (Protective Groups in Organic Synthesis, A. Wiley-Interscience Publication, 1981) or by McOMIE (Protective Groups in Organic Chemistry, Plenum Press, 1973).

The compounds according to the present invention and their synthesis intermediates may be purified by various physical methods. Crystallization or chromatography may be used, for example.

Preferred compounds of general formula (I) are those for which:

X represents a radical chosen from:
  hydrogen,
  hydroxyl, halogen, amino, nitro, mercapto, cyano or carboxyl radicals,
  alkyl, alkoxy, alkylthio, alkylsulphinyl or alkylsulphonyl radicals optionally substituted with 1, 2 or 3 halogen atoms,
  the radicals —NR3R4 with R3 and R4, which are identical or different, chosen from the following radicals:
    hydrogen,
    alkyl optionally substituted with 1, 2 or 3 groups chosen from halogen, hydroxyl, cyano and/or alkoxy,
    —C(O)R5 with R5 chosen from hydrogen or alkyls optionally substituted with a hydroxyl, alkoxy, mercapto or alkylthio radical,
    —(CH2)x-cycloalkyl optionally substituted with a hydroxyl, alkoxy, mercapto, alkylthio, amino, alkylamino, N-alkyl, N-alkylamino or alkyl radical comprising 1, 2, 3 or 4 carbon atoms in the form of a linear or branched chain, x being an integer chosen from 0, 1, 2, 3 and 4,
  the radicals of formula:

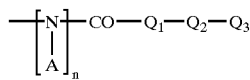

in which:
    n is an integer chosen from 0 and 1,
    when n=1, then A represents either a hydrogen atom or a substituent CO—Q1—Q2—Q3,
    Q1 represents a radical oxy(—O—), —NH—,

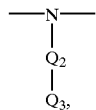

or alternatively:

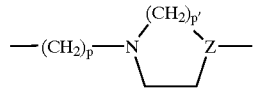

p and p' being integers chosen, independently of each other, from 0, 1, 2 and 3 and Z representing a —CH—, —N— or alternatively oxy group,
    Q2 represents either a group —(CH2)q—, q being an integer chosen from 0, 1, 2, 3 and 4, or a group —(CH2—CH2—O)r—, r being an integer chosen from 2, 3 and 4, and
    Q3 represents a hydrogen atom or a radical chosen from hydroxyl, methoxy, —O—CO—X1, —NHX2 and —N(X1)X2, X1 and
    X2, which are identical or different, representing an alkyl radical or X1 and X2 being linked such that they form, together with the nitrogen atom to which they are attached, an azacycloalkyl radical comprising 3, 4, 5, 6, 7, 8, 9 or 10 members and being capable, in addition, of comprising 1, 2 or 3 heteroatoms chosen from oxygen, sulphur and/or nitrogen,
  it being possible for the substituents —CO—Q1—Q2—Q3 to be identical or different within the same unit of formula [N(A)]n—CO—Q1—Q2—Q3, and
  the radicals of formula:

in which the ring formed with the nitrogen atom comprises 3, 4, 5, 6, 7, 8, 9 or 10 members and may, in addition, comprise 1, 2 or 3 heteroatoms chosen from oxygen, sulphur and/or nitrogen, it being possible for the said ring to also be bridged by an alkyl, to be gem dialkylated or substituted with 1, 2 or 3 groups chosen from hydroxyl, oxo, alkyl and/or alkoxy radicals or with a group —CO—Q1—Q2—Q3 as defined above, R represents a radical chosen from:
  alkyl, alkenyl, alkynyl, 2-, 3- or 4-pyridylalkyl radicals, it being possible for the said pyridyls to be optionally substituted once, twice or three times with alkyl, alkoxy, hydroxyl, halogen and/or amino radicals,
  the radicals of the following formulae:

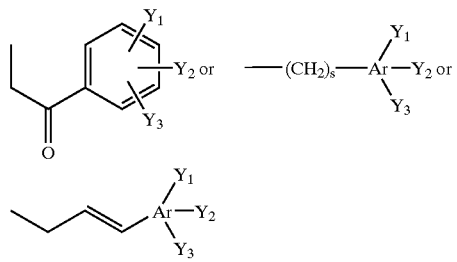

in which:
    s is an integer chosen from 1, 2 and 3,
    Ar represents a phenyl or pyridyl radical,
    Y1, Y2 and Y3, which are identical or different, are radicals chosen from:
      hydrogen, hydroxyl, mercapto, amino, nitro, halogen, —C(O)R6, —C(O)OR6, —C(O)NR6R7, —NR6R7 or —(CH2)t—CN, t being an integer chosen from 0, 1 and 2, and R6 and R7, which are identical or different, representing a hydrogen or an alkyl radical or alternatively R6 and R7 being linked such that they form, together with the nitrogen atom to which they are attached, an azacycloalkyl radical comprising 4, 5, 6 or 7 members and which may comprise, in addition, 1, 2 or 3 heteroatoms chosen from nitrogen, oxygen and/or sulphur, alkyl or alkoxy optionally substituted with 1, 2 or 3 halogen atoms, R1 and R2 represent:

alkyl radicals which are identical or different, or alternatively, R1 and R2 are linked such that they form, together with the nitrogen atom to which they are attached, an azacycloalkyl radical comprising 4, 5, 6 or 7 members and which may comprise, in addition, 1, 2 or 3 heteroatoms chosen from oxygen, sulphur and/or nitrogen, it being possible for the said ring thus formed to be optionally bridged by an alkyl, to be gem dialkylated or substituted with 1, 2 or 3 groups chosen from hydroxyl, oxo, alkyl, alkoxy or phenylalkyl radicals and/or a group —CO—Q1—Q2—Q3 as defined above, it being possible for two of the atoms of the said ring thus formed to also form part of another ring chosen from phenyl and heteroaryl having 4, 5, 6, 7 or 8 members and comprising, in addition, 1, 2, 3 or 4 heteroatoms chosen from oxygen, sulphur and/or nitrogen, and their regioisomers, their salts and their solvates if they exist.

Still more preferred compounds are those of general formula (I) for which:

X represents a radical chosen from:

hydrogen, hydroxyl, halogen or amino radicals, alkyl radicals optionally substituted with 1, 2 or 3 halogen atoms, the radicals —NR3R4 with R3 and R4, which are identical or different, chosen from the following radicals:

hydrogen, alkyl or alternatively

R3 represents a hydrogen atom and R4 represents a group —C(O)R5 with R5 chosen from alkyls optionally substituted with a hydroxyl, alkoxy, mercapto or alkylthio radical R represents a radical chosen from:

alkyl, alkenyl or 3-pyridylmethyl radicals, benzyl optionally substituted with a group —(CH2)t—CN, t being an integer chosen from 0, 1 and 2 or the radicals of formula:

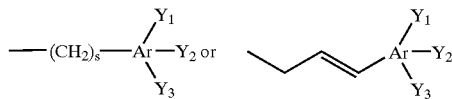

in which:

s is an integer chosen from 1, 2 and 3

Ar represents a phenyl or pyridyl radical,

Y1, Y2 and Y3, which are identical or different, represent depending on the cases:

hydrogen or the methoxy radical,

Y1 and Y2 represent hydrogen and Y3 represents an alkoxy radical or a halogen atom, or alternatively Y1 represents hydrogen and Y2 and Y3 represent an alkoxy radical, R1 and R2 represent:

alkyl radicals which are identical or different, or alternatively, R1 and R2 are linked such that they form, together with the nitrogen atom to which they are attached, an azacycloalkyl radical comprising 4, 5, 6 or 7 members and being capable, in addition, of comprising 1, 2 or 3 heteroatoms chosen from oxygen, sulphur and/or nitrogen, their regioisomers, their salts and their solvates if they exist.

According to a particularly preferred aspect, the compounds according to the present invention are chosen from those of general formula (I) for which:

X represents a hydrogen atom, a halogen atom, an alkyl radical or an alkylamino radical, R represents a radical chosen from the radicals of formula:

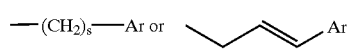

in which s is an integer chosen from 1, 2 and 3 and Ar represents a phenyl or pyridyl radical, R1 and R2 represent:

alkyl radicals which are identical or different, or alternatively, R1 and R2 are linked such that they form, together with the nitrogen atom to which they are attached, an azacycloalkyl radical comprising 4, 5, 6 or 7 members and which may, in addition, comprise 1, 2 or 3 heteroatoms chosen from oxygen, sulphur and/or nitrogen, their regioisomers, their salts and their solvates if they exist.

Most particularly preferred are the compounds according to the present invention which are chosen from those of general formula (I) for which:

X represents a hydrogen atom, a halogen atom, an alkyl radical or an alkylamino radical, R represents a radical chosen from the radicals of formula:

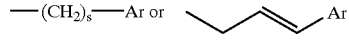

in which s is an integer chosen from 1, 2 and 3 and Ar represents a phenyl or pyridyl radical, and R1 and R2 are either identical and represent methyl radicals, or R1 and R2 are linked such that they form, together with the nitrogen atom to which they are attached, a pyrrolidine or azepan radical, their regioisomers, their salts and their solvates if they exist.

The present invention finally relates more specifically to the triazolo[4,3-a]pyrido[2,3-d]pyrimidin-5-one derivatives chosen from 1-(azepin-1-yl)-4-benzyl-4H-triazolo-[4,3-a] pyrido [2,3-d]pyrimidin-5-one, 1-(azepin-1-yl)-4-cinnamyl-4H-triazolo[4,3-a]pyrido [2,3-d]pyrimidin-5-one, 4-benzyl-1-(pyrrolidin-1-yl)-4H-triazolo[4,3-a]pyrido [2,3-d] pyrimidin-5-one, 4-(3-pyrridinylmethyl)-1-(pyrrolidin-1-yl)-4H-triazolo [4,3-a]pyrido[2,3-d]pyrimidin-5-one, and 4-benzyl-1-dimethylamino-4H-triazolo [4,3-a]pyrido[2,3-d] pyrimidin-5-one, their regioisomers, their salts and their solvates if they exist.

For all the compounds of general formula (I) as presented above, the substituent X in the general formula (I) is preferably at position −7 on the pyridine ring, regardless of its meaning.

The compounds of general formula (I) may optionally, in some cases, be converted to physiologically acceptable salts, in particular to nontoxic and pharmaceutically utilizable salts. More precisely, the compounds of formula (I) according to the invention may be, in some cases, converted to salts with inorganic acids such as, for example, hydrochloric acid, sulphuric acid, phosphoric acid and with organic carboxylic acids or sulphonic acids such as, for example, acetic acid, citric acid, benzoic acid, maleic acid, fumaric acid, tartaric acid, methanesulphonic acid or p-toluenesulphonic acid. These salts may be prepared from the compounds of general formula (I) according to the customary procedures well known to persons skilled in the art, for example by combining an organic or inorganic acid in a solvent or a dispersant, or else according to another alternative from other salts by anion or cation exchange. More generally, persons skilled in the art may refer, for example, to the publication "Pharmaceutical salts" by Berge S. M. et al. (J. Pharm. Sci., 1997, 66, 1–19).

In addition to the salts of the compounds of formula (I), the present invention also relates to other pharmaceutically acceptable forms and derivatives of the compounds of general formula (I) such as the solvates, in particular the hydrates. According to another particular aspect, the invention also relates to the regioisomers (or position isomers) of the compounds according to the present invention, namely compounds of formula:

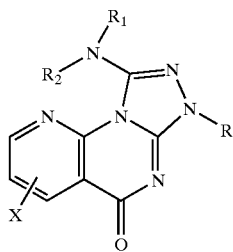

in which X, R, R1 and R2 are as defined above for the compounds of general formula (I). These regioisomers may in particular be obtained in the form of a mixture with the compounds of formula (I) during the last step of synthesis as described above. The two regioisomers may then be separated using conventional separation techniques, in this case, for example by chromatography.

According to yet another aspect of the present invention, it is possible to envisage mixtures of compounds of formula (I), and, where appropriate, mixtures of their salts, solvates or of their regioisomers in any ratios.

The present invention also relates to compositions which can be used in human or veterinary medicine comprising, as active ingredient, at least one compound of general formula (I). According to a preferred aspect, the compositions according to the invention comprise, in addition, a pharmaceutically acceptable vehicle, in general one or more compatible and pharmaceutically acceptable diluents and/or adjuvants (for example buffers, flavouring agents, binders, surfactants, thickeners, preservatives, and the like). The compositions are prepared according to common methods well known to persons skilled in the art. They generally comprise 0.5% to 60% by weight of active ingredient and 40% to 99.5% by weight of appropriate pharmaceutical vehicle. In addition, the compositions of the present invention are prepared in forms compatible with the desired route of administration. Numerous routes of administration may be envisaged. For example, the compositions according to the invention may be formulated for administration by the topical, oral, parenteral, nasal, pulmonary, intravenous, intra-muscular, subcutaneous, transdermal, intratracheal or intraperitoneal route, or the like.

When an administration by the oral route is envisaged, the compositions according to the invention may be provided, for example, in the form of tablets, cachets, sachets of powder for oral suspension, gelatin capsules, gastro-resistant gelatin capsules, prolonged-release forms, emulsions, lyophilisates to be melted under the tongue or oral solutions. The powders, tablets, cachets or encapsulated forms preferably contain from 5% to 70% of active ingredient. Appropriate carriers are, for example, magnesium carbonate, magnesium stearate, talc, lactose, sugar, pectin, dextrin, starch, gum tragacanth, methylcellulose, carboxymethylcellulose sodium, low-melting-point wax or cocoa butter. The tablets, powders, cachets and capsules may also be used as a unit dose for administration by the oral route.

In the case of powders, the carrier is preferably a finely divided solid, which is in the form of a mixture with the finely divided compound of general formula (I) according to the invention. In the case of tablets, the active compound is mixed with a carrier having the required binding properties in an appropriate quantity, and then the mixture is compressed to the required shape and size.

In the case of aqueous solutions for administration by the oral route, they may be prepared by dissolving the active ingredient and adding, if necessary, colourings, flavour modifiers, flavourings, stabilizers, thickening agents or any other appropriate adjuvant. By way of example, the active ingredient may be dispersed in the form of a finely divided powder in water with a viscous material such as synthetic gums, resins, methylcellulose, carboxymethylcellulose sodium, and other suspending agents well known in the galenic field.

When administration by the parenteral route is envisaged, the compositions according to the invention may be provided, for example, in the form of aqueous solutions, water/cosolvent solutions, solutions using one or more solubilizers, colloidal suspensions, emulsions, nanoparticulate suspensions which can be used for injection of prolonged-release forms, dispersed forms or liposomes. Sterile solutions of water and/or of propylene glycol of the active ingredient may be mentioned as examples of liquid preparations appropriate for administration by the parenteral route. The liquid preparations may also be formulated in the form of aqueous solutions of polyethylene glycol. All these presentations can be more particularly used in the context of administration by the intravenous route. In the precise case of administration by the subcutaneous or intramuscular route, the compositions according to the invention may, in addition, be provided, for example, in the form of suspensions, dispersed forms, prolonged-release gels and prolonged-release implants.

When administration by the topical route is envisaged, the compositions according to the invention may be provided in numerous forms. Among the most common topical forms are creams, gels (aqueous phases gelled with polymers), patches which are dressings to be stuck directly on the skin and which may be used for treating dermatosis without percutaneous penetration of the active substance, sprays, emulsions and solutions.

When administration by the pulmonary route is envisaged, the compositions according to the invention may be provided in the form of aerosol solutions or powders for inhalers, although other forms may also be considered. When the compositions are aerosols, for use in the form of liquid aerosols, the compositions may be stable sterile solutions or solid compositions dissolved at the time of use in apyrogenic sterile water, in serum or any other pharmaceutically acceptable vehicle. For use in the form of dry aerosols intended to be directly inhaled, the active ingredient is finely divided and combined with a water-soluble solid vehicle or diluent. In the case of aerosols, the active ingredient is finely divided and combined with a water-soluble solid vehicle or diluent having a particle size of 30 µm to 80 µm, for example dextran, mannitol or lactose.

When administration by the nasal route is envisaged, the compositions according to the invention are provided especially in the form of solutions or suspensions for drops, or alternatively other forms may also be considered.

When administration by the rectal route is envisaged, the compositions according to the invention are provided especially in the form of suppositories or gels, although other forms can also be considered. In the case of suppositories, a low-melting-point wax, such as a mixture of fatty acid glycerides and cocoa butter is first melted, then the active ingredient is dispersed therein, for example by mechanical stirring. The homogeneous molten mixture is then poured into moulds of appropriate shape and then allowed to cool and solidify.

Another important category of pharmaceutical dosage form which may be used in the context of the present invention relates to the forms which make it possible to improve the solubility of the active ingredient. By way of example, it is possible to envisage the use of aqueous solutions of cyclodextrin, and more particularly of the forms comprising hydroxypropyl β-cyclodextrin. A detailed review of this type of pharmaceutical dosage forms is presented in Journal of Pharmaceutical Sciences, 1996, 85(11), 1142–69).

The various pharmaceutical dosage forms recommended above are also described in detail in the book "Pharmacie galénique" by A. LEHIR (Ed. Masson, 1992, 6th edition).

In general, the doctor will determine the dosage which he judges most appropriate according to the age of the patient, his state of health, his weight, his gender, the nature and the seriousness of the condition to be treated, the possible combination with other treatments, and any other factor specific to the subject to be treated and to the disease in question. The daily dosage in humans is usually between 2 mg and 1 g of active product (for a man of average weight, that is to say weighing about 70 kg) which may be administered in one or several doses.

The compounds of formula (I) according to the invention, and where appropriate their salts and their derivatives, and the compositions comprising them possess properties inhibiting PDE4 and/or the release of TNFα. The compounds of the invention may thus be used as a medicament, in particular for the treatment or prevention of conditions involving the production of TNFα and in particular the treatment or prevention of inflammatory conditions of the asthma or chronic obstructive pulmonary disease (COPD) type. However, the compounds of the invention may also be used as a medicament, in particular for the treatment or prevention of conditions including cancer, acquired immunodeficiency syndrome, fibrosis, excessive formation of scars including excessive formation of scars in the dermis, such as the normal or abnormal formation of scars in the dermis after a surgical operation or a wound, osteoarthritis, osteoporosis, multiple sclerosis, anxiety, depression, atopic dermatitis, rheumatoid arthritis, septic shock, immune diseases including systemic lupus erythematosis, psoriasis, graft rejection, allergic rhinitis and post-ischaemic lesion diseases, pulmonary hypertension, congestive heart failure, acute respiratory distress syndrome, chronic inflammatory bowel diseases (irritable bowel syndrome) such as Crohn's disease and ulcerative colitis. According to another aspect of the invention, the compounds of formula (I) may be used for the manufacture of a medicament for treating diseases which may be treated by virtue of an inhibition of the PDE4 enzyme and the resulting increase in the cAMP level, in particular the diseases cited above, and more specifically inflammatory conditions of the asthma or chronic obstructive pulmonary disease (COPD) type.

The present invention thus provides a particularly advantageous method for the treatment of diseases by administering a compound of formula (I) or a composition comprising it under the conditions defined above. More particularly, this method is applicable to diseases which may be treated/prevented by virtue of an inhibition of the PDE4 enzyme and the resulting increase in the cAMP level, such as the diseases mentioned above and more specifically inflammatory conditions of the asthma or chronic obstructive pulmonary disease (COPD) type. Thus, another subject of the present invention relates to methods for the treatment or prevention of a condition by virtue of an inhibition of the PDE4 enzyme and the resulting increase in the cAMP level, the said method comprising the administration, to a patient, of an effective concentration of a compound of formula (I) as defined above.

In addition to the preceding features, the present invention also comprises other characteristics and advantages which will emerge from the examples which follow, and which should be considered as illustrating the invention without limiting the scope thereof. In particular, there is proposed, without limitation, various operating protocols and reaction intermediates which can be used to prepare the compounds of general formula (I). Of course, it is within the capability of persons skilled in the art to draw inspiration from these protocols and/or intermediate products to develop similar procedures so as to give other compounds of general formula (I) according to the invention.

EXAMPLES

Preparation of 3-benzyl-2-thione-1,2,3,4-tetrahydropyrido[2,3-d]pyrimidin-4-one (Intermediate 1A)

53 ml of benzyl isothiocyanate (398 mmol) are added dropwise, over 10 minutes, with stirring, to a suspension of 50 g of 2-aminonicotinic acid (362 mmol) in 600 ml of pyridine. Once the addition is complete, the reaction mixture is heated at the reflux temperature for 24 hours. The insoluble solid obtained is filtered and the filtrate thus obtained is poured over a water (2.5 litres)/ice (500 g) mixture. The insoluble paste thus obtained is triturated several times in ethanol. The resulting crude crystals are then dried at 50° C. for 48 hours. 46.4 g of 3-benzyl-2-thione-1,2,3,4-tetrahydropyrido[2,3-d]pyrimidin-4-one are thus obtained (yield: 47%), which is used directly without further purification in the next reaction steps.

1H NMR (DMSO-d6): 5.65 (s, 2H); 7.2–7.4 (m, 6H); 8.35 (m, 1H); 8.8 (m, 1H); 13.5 (m, 1H)

Preparation of 3-benzyl-6-methyl-2-thione-1,2,3,4-tetrahydropyrido[2,3-d]pyrimidin-4-one (Intermediate 1B)

In the same manner as for the preparation of intermediate 1A, the reaction of 20 g of 2-aminopyridyl-3-carboxylic acid (111 mmol) which are synthesized in accordance with the method described in J. Het. Chem. (1982, 19, 1461) with 15 ml of benzyl isothiocyanate (111 mmol) in 200 ml of pyridine gives, after crystallization from ethanol, 24 g of crude 3-benzyl-6-methyl-2-thione-1,2,3,4-tetrahydropyrido[2,3-d]pyrimidin-4-one (yield: 77%) which is used directly without further purification in the next reaction steps.

Preparation of 3-benzyl-2-hydrazino-3,4-dihydropyrido[2,3-d]pyrimidin-4-one (Intermediate 2A)

80 ml of hydrazine hydrate (1.4 mol) are added dropwise, with stirring, to a suspension of 46.4 g of 3-benzyl-2-thione- 3,4-dihydropyrido[2,3-d]pyrimidin-4-one (172.5 mmol) in 800 ml of ethanol. The reaction mixture is then heated at the reflux temperature for 6 hours, under an argon stream. The reaction mixture is then cooled and the solvent is concentrated until a residual volume of 200 ml is obtained. The crude solid which precipitates is then filtered and then washed several times with cold ethanol so as to give 33.3 g of a whitish solid (yield: 72%).

Melting point: 139° C.

1H NMR (DMSO-d6): 5.25 (s, 2H); 7.1–7.3 (m, 6H); 8.25 (m, 1H); 8.75 (m, 1H)

Preparation of 3-benzyl-2-hydrazino-6-methyl-3,4-dihydropyrido[2,3-d]pyrimidin-4-one (Intermediate 2B)

In the same manner as for the preparation of intermediate 2A, the reaction of 24 g of 3-benzyl-6-methyl-2-thione-3,4-dihydropyrido[2,3-d]pyrimidin-4-one (85 mmol) with 39 ml of hydrazine hydrate (678 mmol) in 400 ml of ethanol gives, after crystallization from ethanol, 20.6 g of crude product (yield: 86%) which is used directly without further purification in the next reaction steps.

Preparation of 4-benzyl-4H-triazolo[4,3-a]pyrido[2,3-d]pyrimidin-5-one (Intermediate 3A)

A solution of 33.5 g of 3-benzyl-2-hydrazino-3,4-dihydropyrido[2,3-d]pyrimidin-4-one (125 mmol) in 1 litre of chloroform is cooled to 5° C. and 92.6 g of concentrated ethyl orthoformate (625 mmol) in sulphuric acid (0.5 ml) are added dropwise, with stirring, while the temperature is maintained below 5° C. The reaction mixture is then stirred for 6 hours at room temperature. An additional 0.5 ml of concentrated sulphuric acid is then added and the solution is stirred overnight at room temperature. The organic phase is then poured into a sodium bicarbonate solution, and then stirred, separated, washed several times with water and brine, and finally dried over anhydrous sodium sulphate. After concentration under reduced pressure, a coloured crude product is obtained which is stirred in cold ethanol so as to give 32.4 g of pure product in thin-layer chromatography (TLC) (yield: 93%).

Melting point: 222° C.

1H NMR (CDCl3): 5.5 (s, 2H); 7.25–7.35 (m, 3H); 7.5 (m, 1H); 7.65 (m, 2H); 8.65 (m, 1H); 8.75 (m, H); 9.05 (s, 1H)

Preparation of 4-benzyl-7-methyl-4H-triazolo[4,3-a]pyrido[2,3-d]pyrimidin-5-one (Intermediate 3B)

In the same manner as for the preparation of intermediate 3A, the cyclization of 20.6 g of 3-benzyl-2-hydrazino-6-methyl-3,4-dihydropyrido[2,3-d]pyrimidin-4-one (73 mmol) with 54.3 g of ethyl orthoformate (36.6 mmol) in chloroform gives, after crystallization of the crude product from ethanol, 18.5 g of a pure solid in TLC (yield: 87%).

Melting point: 226° C.

1H NMR (DMSO-d6): 2.6 (s, 3H); 5.5 (s, 2H); 7.4 (m, 3H); 7.6 (m, 2H); 8.55 (s, 1H); 8.9 (s, 1H); 9.5 (s, 1H)

Preparation of 4-benzyl-1-bromo-4H-triazolo[4,3-a]pyrido[2,3-d]pyrimidin-5-one (Intermediate 4)

Under an inert atmosphere, a bromine solution (18.7 g) in 5 ml of chloroform is added dropwise to a solution of 10.0 g of intermediate 3A (36 mmol) in 250 ml of chloroform. Once the addition is complete, the stirring is maintained at room temperature for 2 hours. The insoluble solid is separated by filtration and washed with several portions of methylene chloride. The combined organic phases are then washed several times successively with a sodium bicarbonate solution and water to neutral pH, and then dried over sodium sulphate and evaporated to dryness so as to give 7 g of solid (yield: 56%).

1H NMR (CDCl3): 5.5 (s, 2H); 7.3 (m, 3H); 7.55 (m, 1H); 7.65 (m, 2H); 8.7 (m, 1H); 8.85 (m, 1H)

Example 1

Preparation of 1-(azepin-1-yl)-4-benzyl-4H-triazolo[4,3-a]pyrido[2,3-d]pyrimidin-5-one A suspension of 0.8 g of 4-benzyl-1-bromo-4H-triazolo[3,4-a]pyrido[2,3-d]pyrimidin-4-one (2.2 mmol) in 4 ml of hexamethyleneimine is stirred and heated at the reflux temperature for 20 hours under an inert atmosphere. The excess amine is evaporated under vacuum and the residue is partitioned between 25 ml of 2 N aqueous hydrochloric acid solution and 50 ml of ethyl acetate. The organic phase is separated, washed with water, dried over sodium sulphate and finally concentrated to dryness to give 0.7 g of a crude solid which is recrystallized from ethanol to give 0.47 g of a yellow solid (yield: 57%).

Melting point: 178° C.

TLC: CH2Cl2 97/CH3OH 3; Rf=0.65

1H NMR (DMSO-d6): 1.7–1.8 (m, 4H); 1.9–2 (m, 4H); 3.6–3.65 (m, 4H); 5.45 (s, 2H); 7.25–7.35 (m, 3H); 7.45–7.5 (m, 4H); 7.6–7.65 (m, 2H); 8.65 (m, 2H); 8.9 (m, 2H)

Example 2

Preparation of 4-benzyl-1-(pyrrolidin-1-yl)-4H-triazolo[4,3-a]pyrido[2,3-d]pyrimidin-4-one According to a procedure similar to that described in Example 1, the condensation of 4.0 g of 4-benzyl-1-bromo-4H-triazolo[3,4-a]pyridopyrimidin-4-one (11.2 mmol) with 1.6 g of pyrrolidine (22.5 mmol) in the presence of 1.9 g of potassium bicarbonate (22.5 mmol) in 60 ml of dimethylformamide gives, after chromatography on a silica column of the crude product (ethyl acetate/cyclohexane 70/30), 2.7 g of a pure solid in TLC (yield: 71%).

Melting point: 204° C.

1H NMR (CDCl3): 2 (m, 4H); 3.6 (m, 4H); 5.45 (s, 2H); 7.25 (m, 3H); 7.45 (m, 1H); 7.7 (m, 2H); 8.6 (m, 1H); 8.8 (m, 1H)

Example 3

Preparation of 4-benzyl-1-dimethylamino-4H-triazolo[4,3-a]pyrido[2,3-d]pyrimidin-5-one According to a procedure similar to that described in Example 1, the condensation of 1.5 g of 4-benzyl-1-bromo-4H-triazolo[3,4-a]pyrido[2,3-d]pyrimidin-4-one (4.2 mmol) with 0.7 g of dimethylamine hydrochloride (8.4 mmol) in the presence of 1.7 g of potassium carbonate (12.6 mmol) in 30 ml of dimethylformamide gives 0.65 g of a pure solid in TLC (yield: 50%) after chromatography on a silica column (eluent: dichloromethane/methanol 98/2) and crystallization from ethanol.

Melting point: 160° C.

TLC: CH2Cl2 95/CH3OH 5; Rf=0.3

1H NMR (CDCl3): 3 (s, 6H); 5.45 (s, 2H); 7.3 (m, 3H); 7.45 (m, 1H); 7.7 (m, 2H); 8.65 (m, 1H); 8.8 (m, 1H)

Example 4

Preparation of the Regioisomers 1-(azepin-1-yl)-4-cinnamyl-4H-triazolo [4,3-a]pyrido[2,3-d]pyrimidin-5-one and 1-(azepin-1-yl)-3-cinnamyl-3H-triazolo [4,3-a]pyrido[2,3-d]pyrimidin-5-one 1.21 g of 1-azepinyl-4-benzyl-4H-triazolo[3,4-a]pyrido[2,3-d]pyrimidin-5-one (3.2 mmol) and 2.56 g of aluminium chloride (19.2 mmol) in 30 ml of benzene are heated to 50° C. The reaction mixture is stirred at this temperature for half an hour, and then carefully poured over a water/ice mixture. After further stirring for half an hour, the aqueous phase is extracted twice with methylene chloride. The combined organic phases are washed, dried over sodium sulphate and concentrated to give a crude solid which is purified by chromatography on a silica column (eluent: dichloromethane/methanol 97.5/2.5). The pure fractions thus obtained are combined and evaporated to give 0.83 g of a pure beige compound in TLC (yield: 91%).

1H NMR (DMSO-d6): 1.7 (m, 4H); 1.9 (m, 4H); 3.5 (m, 4H); 7.6 (m, 1H); 8.5 (m, 1H); 8.8 (m, 1H); 12.75 (m, 1H)

0.83 g of 1-azepinyl-4H-triazolo[4,3-a]pyrido[2,3-d]pyrimidin-5-one obtained in the preceding step (2.9 mmol) is dissolved in 10 ml of 1,2-dimethoxyethane. 0.069 g of sodium hydride (2.9 mmol) is added, and the reaction mixture is stirred at room temperature for 30 minutes. 0.57 g of cinnamyl bromide (2.9 mmol) is added in a single portion and the reaction mixture is heated at 100° C., while stirring, for 4 hours. The solvent is evaporated to dryness under vacuum and the residue is recovered in a mixture of water and ethyl acetate. The organic phase is then separated, washed with a saturated sodium chloride solution, dried over sodium sulphate and concentrated so as to give 1.1 g of a crude mixture of the two regioisomers. These isomers are separated by chromatography on a silica column (eluent: methylene chloride/methanol 98.5/1.5). There are thus obtained, in the order of elution:

0.19 g (yield: 16%) of pure 1-(azepin-1-yl)-4-cinnamyl-4H-triazolo[3,4-a]pyrido [2,3-d]pyrimidin-5-one in TLC (Rf=0.5).

1H NMR (DMSO-d6): 1.75 (m, 4H); 1.95 (m, 4H); 3.6 (m, 4H); 5.05 (m, 2H); 6.4–6.55 (m, 1H); 6.9 (m, 1H); 7.2–7.45 (m, 7H); 8.7 (m, 1H); 8.8 (m, 1H)

0.58 g (yield: 58%) of pure 1-(azepin-1-yl)-3-cinnamyl-3H-triazolo[4,3-a]pyrido [2,3-d]pyrimidin-5-one in TLC (Rf=0.3).

1H NMR (DMSO-d6): 1.7–1.8 (m, 4H); 1.9 (m, 4H); 3.6 (m, 4H); 4.9 (m, 2H); 6.3–6.4 (m, 1H); 6.7–6.8 (m, 1H); 7.2–7.5 (m, 7H); 8.7–8.8 (m, 2H)

Example 5
Preparation of 4-(3-pyridylmethyl)-1-(pyrrolidin-1-yl)-4H-triazolo[4,3-a]pyrido [2,3-d]pyrimidin-5-one According to a procedure similar to that described in Example 4, 2.4 g of 1-pyrrolidinyl-4-benzyl-4H-triazolo[3,4-a]pyrido[2,3-d]pyrimidin-5-one obtained in Example 2 (6.9 mmol) are debenzylated with 5.5 g of aluminium chloride (41.6 mmol) in toluene to give, after purification by chromatography on a silica column (eluent: dichloromethane/methanol/ammonium NH4OH 90/9/1), 0.5 g of a pure product in TLC (yield: 30%).

Melting point: 225° C.

1H NMR (DMSO-d6): 2.0 (m, 4H); 3.6 (m, 4H); 7.7 (m, 1H); 8.6 (m, 1H); 8.9 (m, 1H); 12.8 (s, 1H)

0.49 g of 1-(pyrrolidin-1-yl)-4H-triazolo[3,4-a]pyridopyrimidin-4-one obtained in the preceding step (1.91 mmol) is dissolved in 30 ml of dimethyl sulphoxide (DMSO) and 0.32 g of potassium hydroxide (5.7 mmol) is added. The solution obtained is stirred at room temperature, under an inert atmosphere, for 1 hour. 0.28 g of 3-pyridylmethyl chloride (1.7 mmol) is then added in a single portion while the temperature is maintained below 20° C. and stirring for a further 4 hours. The solvent is then evaporated under vacuum and the residue is extracted with a mixture of water and ethyl acetate. The organic phase is then separated, washed with a saturated sodium chloride solution, dried over sodium sulphate and concentrated to dryness to give 0.59 g of a crude product which is purified by chromatography on a silica column (eluent: methylene chloride/methanol/ammonia 95/5/0.1). The pure fractions are then combined and evaporated to give 0.14 g of a pure yellow product (yield: 24%) which is crystallized from an ethanol/isopropyl ether mixture.

Melting point: 173° C.

1H NMR (CDCl3): 2 (m, 4H); 3.6 (m, 4H); 5.4 (s, 2H); 7.2 (m, 1H); 7.45 (m, 1H); 8 (m, 1H); 8.5 (m, 1H); 8.65 (m, 1H); 8.8 (m, 1H); 8.9 (s, 1H)

Example 6
Evaluation of the in vitro Activity of the Compounds of the Invention

The capacity of the compounds of formula (I) to inhibit cyclic nucleotide phosphodiesterases is evaluated by measuring their IC50 (concentration necessary to inhibit 50% of the enzymatic activity). In the case of the PDE4 enzymes, this value is often compared with the IC50 for rolipram (INN), a reference inhibitor of PDE4 enzymes.

The type 4 phosphodiesterases (PDE4) are obtained from a cytosolic preparation extracted from a cell line of human origin U937 according to the method adapted from T. J. Torphy et al. (J. Pharm. Exp. Ther., 1992, 263, 1195–205).

The other types of phosphodiesterase are obtained during a partial purification by FPLC on a Mono Q column (anion exchange column) according to a method adapted from Lavan B. E. et al. (Biochemical Pharmacology, 1989 38(22), 4123–36) and from Silver P. J. et al. (Eur. J. Pharmacol., 1988, 150, 85–94), either from cell lines of human origin for PDE1 (monocyte line TPH1) and PDE5 (line obtained from an adenocarcinoma MCF7), or from dog aorta for PDE3, or for human PDE3A from a cloning of genes into insect cells SF21 in baculovirus, according to the method adapted from Luckow V. A. et al. (Recomb. DNA Technol. & Appl., Eds. Prokop, Bajpa R. K. & Ho C. S., 1991, 97–152).

The measurement of the enzymatic activity of the various types of PDE, and in particular of the PDE4 enzymes, is carried out according to a method adapted from W. J. Thompson et al. (Advances in Cyclic Nucleotide Research, Ed. G. Brooker et al., Raven Press, NY, 1979, 10, 69–92).

In the present case, the substrate used is cAMP at a concentration of 0.25 µM. The enzymatic reaction used is stopped after 10 minutes. In order to determine their IC50, the compounds according to the present invention were tested for 8 to 11 concentrations in a concentration range of between 0.02 nM and 100 µM.

It was thus found that the products of the invention possess an IC50 of less than or equal to 7 µM.

What is claimed is:
1. A compound of formula I:

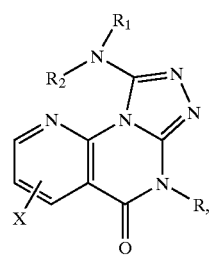

I or a pharmaceutically acceptable salt thereof, wherein:
X is hydrogen, hydroxy, halo, nitro, mercapto, cyano, carboxy, $(C_1-C_6)$alkyl, $(C_1-C_6)$ alkoxy, $(C_1-C_6)$alkylthio, $C_1-C_6)$alkylsulfonyl, $(C_1-C_6)$alkylsulfinyl, $-NR^3R^4$, $-(N-A)_n-C(O)-Q^1-Q^2-Q^3$ or a 3 to 10 membered azacycloalkyl; said alkyl, alkoxy, alkylthio, alkylsulfinyl and alkylsulfonyl in the definition of X being optionally substituted independently with up to three halo atoms; said azacycloalkyl in the definition of X further optionally being bridged by $(C_1-C_6)$alkylenyl; said azacycloalkyl in the definition of X being optionally gem-dialkylated or independently substituted with up to three hydroxy, oxo, $(C_1-C_6)$alkyl, $(C_1-C_6)$alkoxy or —C(O)—$Q^1$—$Q^2$—$Q^3$;

R is $(C_1-C_6)$alkyl; $(C_1-C_6)$alkenyl; 2-pyridyl$(C_1-C_6)$alkyl; 3-pyridyl$(C_1-C_6)$alkyl; 4-pyridyl$(C_1-C_6)$alkyl, said pyridyls being optionally substituted independently by up to three $(C_1-C_6)$alkyl, $(C_1-C_6)$alkoxy, hydroxy, halo or amino; or a radical of the formula

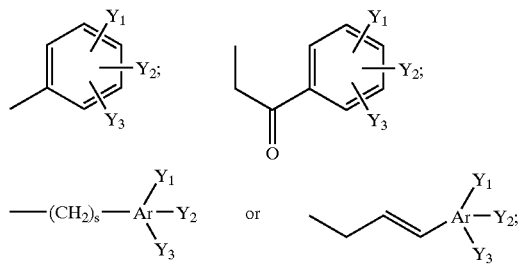

$R^1$ and $R^2$ are taken separately, are different, and are $(C_1-C_6)$alkyl, aralkyl, $(C_3-C_{10})$ cycloalkyl or $(C_3-C_{10})$ cycloalkyl-$(C_1-C_6)$alkyl; or $R^1$ and $R^2$ are taken separately, are identical and are $(C_1-C_6)$alkyl; or $R^1$ and $R^2$ are taken together, with the nitrogen atom to which they are attached, to form a 3 to 7 membered azacycloalkyl; said azacycloalkyl in the definition of $R^1$ and $R^2$ being optionally bridged by $(C_1-C_6)$alkylenyl and optionally gem-dialkylated or substituted with up to three hydroxy, oxo, $(C_1-C_6)$alkyl, $(C_1-C_6)$ alkoxy, phenyl-$(C_1-C_6)$alkyl or —C(O)—$Q^1$—$Q^2$—$Q^3$ $R^3$ and $R^4$ are independently hydrogen; $(C_1-C_6)$alkyl optionally substituted with up to three halo, hydroxy, cyano or $(C_1-C_6)$alkoxy; $R^5$-carbonyl; or $(C_3-C_{10})$ cycloalkyl-$(C_0-C_4)$ alkylenyl optionally substituted with a hydroxy, $(C_1-C_6)$alkoxy, mercapto, $(C_1-C_6)$ alkylthio, amino, N—$(C_1-C_6)$alkylamino, di-N—$(C_1-C_6)$alkylamino or $(C_1-C_4)$alkyl;

$R^5$ is hydrogen or $(C_1-C_6)$alkyl optionally substituted with hydroxy, $(C_1-C_6)$alkoxy, mercapto or $(C_1-C_6)$ alkylthio;

n is 0 or 1;

A is independently hydrogen or —C(O)—$Q^1$—$Q^2$—$Q^3$;

$Q^1$ is independently —O—, —NH—, —N($Q^2$—$Q^3$)— or

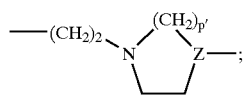

$Q^2$ is independently $(C_0-C_4)$alkylenyl or —(CH$_2$CH$_2$—O)$_r$—;

$Q^3$ is independently hydrogen, hydroxy, methoxy, —O—C(O)—$X^1$, —NH$X^2$ or —N($X^1$)$X^2$;

p and p' are independently , 0, 1, 2 or 3;

Z is independently —CH— or —N—;

r is independently 2, 3 or 4;

$X^1$ and $X^2$ are taken separately and are independently $(C_1-C_6)$alkyl; or $X^1$ and $X^2$ are taken together with the nitrogen atom to which they are attached to form a 3- to 10-membered azacycloalkyl s is 1, 2, 3 or 4;

Ar is a 5- or 6-membered aryl;

$Y^1$, $Y^2$ and $Y^3$ are independently hydrogen, hydroxy, mercapto, amino, nitro, halo, $(C_1-C_6)$alkyl, $(C_1-C_6)$alkoxy, $(C_1-C_6)$alkylthio, $(C_1-C_6)$alkylsulfinyl, $(C_1-C_6)$alkylsulfonyl, —C(O)$R^6$, —C(O)O$R^6$, —C(O)N$R^6R^7$, —N$R^6R^7$, —(CH$_2$)$_t$CN or —(CH$_2$)$_t$—C(O)—$Q^1$—$Q^2$—$Q^3$; said $(C_1-C_6)$alkyl, $(C_1-C_6)$alkoxy, $(C_1-C_6)$alkylthio, $(C_1-C_6)$alkylsulfinyl and $(C_1-C_6)$alkylsulfonyl being optionally substituted independently with up to three halo atoms;

t is independently 0, 1 or 2; and $R^6$ and $R^7$ are taken separately and are independently hydrogen or $(C_1-C_6)$alkyl; or $R^6$ and $R^7$ are taken together with the nitrogen atom to which they are attached to form a 4- to 7-membered azacycoalkyl.

2. A compound of claim 1, or a pharmaceutically acceptable salt thereof, wherein:

R is $(C_1-C_6)$alkyl; $(C_1-C_6)$alkenyl; $(C_1-C_6)$alkynyl; 2-pyridyl$(C_1-C_6)$alkyl; 3-pyridyl $(C_1-C_6)$alkyl; 4-pyridyl$(C_1-C_6)$alkyl, said pyridyls being optionally substituted independently by up to three $(C_1-C_6)$alkyl, $(C_1-C_6)$alkoxy, hydroxy, halo or N$R^3R^4$; or a radical of the formula

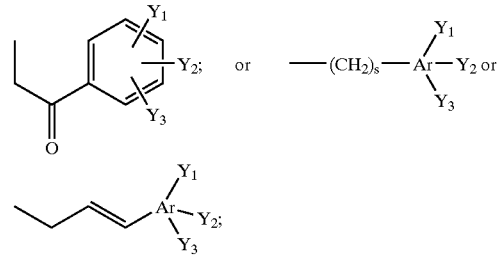

s is 1, 2 or 3; Ar is phenyl a pyridyl; $Y^1$, $Y^2$ and $Y^3$ are independently hydrogen, hydroxy, mercapto, amino, nitro, halo, $(C_1-C_6)$alkyl, $(C_1-C_6)$alkoxy, —C(O)$R^6$, —C(O)O$R^6$, —N$R^6R^7$ or —(CH$_2$)$_t$CN; said $(C_1-C_6)$alkyl and $(C_1-C_6)$ alkoxy in the definition of $Y^1$, $Y^2$ and $Y^3$ being optionally substituted independently with up to three halo atoms; and $R^1$ and $R^2$, when taken separately, are identical and are $(C_1-C_6)$alkyl.

3. A compound of claim 2, or a pharmaceutically acceptable salt thereof, wherein:

X is hydrogen; hydroxy; halo; amino; $(C_1-C_6)$alkyl optionally substituted independently with up to three halo; or —N$R^3R^1$;

$R^3$ and $R^4$ are taken separately and are independently hydrogen or $(C_1-C_6)$alkyl; or $R^3$ and $R^4$ are taken separately and $R^3$ is hydrogen and $R^4$ is —C(O)$R^5$;

$R^5$ is $(C_1-C_6)$alkyl optionally substituted with hydroxy, $(C_1-C_6)$alkoxy, mercapto or $(C_1-C_6)$alkylthio;

R is $(C_1-C_6)$alkyl; $(C_1-C_6)$alkenyl; 3-pyridylmethyl; benzyl optionally substituted with —(CH$_2$)$_t$—CN; or a radical of the formula

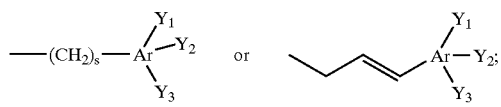

$Y^1$, $Y^2$ and $Y^3$ are independently hydrogen or methoxy; or
$Y^1$ and $Y^2$ are H and $Y^3$ is ($C_1$–$C_6$)alkoxy or halo; or
$Y^1$ is H and $Y^2$ and $Y^3$ are each independently ($C_1$–$C_6$) alkoxy;

$R^1$ and $R^2$ are taken separately and are independently ($C_1$–$C_6$)alkyl; or $R^1$ and $R^2$ are taken together, with the nitrogen atom to which they are attached, to form a 3 to 7 membered azacycloalkyl.

4. A compound of claim 3, or a pharmaceutically acceptable salt thereof, wherein X is hydrogen, halo, ($C_1$–$C_6$)alkyl, or —$NR^3R^4$; $R^3$ is hydrogen and $R^4$ is ($C_1$–$C_6$)alkyl; or $R^3$ is ($C_1$–$C_6$)alkyl and $R^4$ is hydrogen; and R is

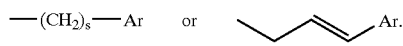

5. A compound of claim 4, or a pharmaceutically acceptable salt thereof, wherein $R^1$ and $R^2$ are each methyl or $R^1$ and $R^2$ are taken together with the nitrogen atom to which they are attached to form a pyrrolidine or azepine.

6. A compound of claim 5, or a pharmaceutically acceptable salt thereof, wherein X is substituted at the 7- position of the pyridine ring.

7. A compound of claim 1, or a pharmaceutically acceptabl salt thereof, which is 1-(azepin-1-yl)-4-benzyl-4H-triazolo-[4,3-a]pyrido [2,3-d]pyrimidin-5-one; 1-(azepin-1-yl)-4-cinnamyl-4H-triazolo[4,3-a]pyrido [2,3-d]pyrimidin-5-one; 4-benzyl-1-(pyrrolidin-1-yl)-4H-triazolo[4,3-a] pyrido [2,3-d]pyrimidin-5-one; 4-(3-pyridinylmethyl)-1-(pyrrolidin-1-yl)-4H-triazolo[4,3-a]pyrido [2,3-d] pyrimidin-5-one; or 4-benzyl-1-dimethylamino-4H-triazolo [4,3-a]pyrido[2,3d]pyrimidin-5-one.

8. A pharmaceutical composition comprising a compound of claim 1 or pharmaceutically acceptable salt thereof.

9. A pharmaceutical composition of claim 8 additionally comprising a pharmaceutically acceptable vehicle.

10. A pharmaceutical composition of claim 9 wherein said pharmaceutically acceptable vehicle is chosen from at least one compatible diluent or adjuvant.

11. A pharmaceutical composition of claim 9 or wherein said compound comprises 0.5% to 60% by weight and said pharmaceutically acceptable vehicle comprises 40% to 99.5% by weight of the total weight of said composition, providing that the sum of said percentages is 100%.

12. A compound of Formula II,

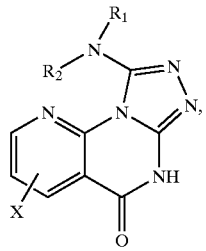

(II)

or a pharmaceutically acceptable salt thereof, wherein:

X is hydrogen, hydroxy, halo, nitro, mercapto, cyano, carboxy, ($C_1$–$C_6$)alkyl, ($C_1$–$C_6$)alkoxy, ($C_1$–$C_6$) alkylthio, ($C_1$–$C_6$))alkylsulfinyl, ($C_1$–$C_6$)alkylsulfonyl, —$NR^3R^4$, —$(N—A)_n$—$C(O)$—$Q^1$—$Q^2$—$Q^3$ or a 3 to 10 membered azacycloalkyl; said alkyl, alkoxy, alkylthio, alkysulfinyl and alkylsulfonyl in the definition of X being optionally substituted independently with up to three halo; said azacycloalkyl in the definition of X further optionally being bridged by ($C_1$–$C_6$) alkylenyl; said azacycloalkyl in the definition of X being optionally gem-dialkylated or independently substituted with up to three hydroxy, oxo, ($C_1$–$C_6$)alkyl, ($C_1$–$C_6$)alkoxy or $C(O)$—$Q^1$—$Q^2$—$Q^3$;

$R^1$ and $R^2$ are taken separately, are different, and are ($C_1$–$C_6$)alkyl, aralkyl, ($C_3$–$C_{10}$) cycloalkyl or ($C_3$–$C_{10}$) cycloalkyl-($C_1$–$C_6$)alkyl; or $R^1$ and $R^2$ are taken separately, are identical and are ($C_1$–$C_6$)alkyl; or $R^1$ and $R^2$ are taken together, with the nitrogen atom to which they are attached, to form a 3 to 7 membered azacycloalkyl; said azacycloalkyl in the definition of $R^1$ and $R^2$ being optionally bridged by ($C_1$–$C_6$)alkylenyl and optionally gem-dialkylated or substitut with up to three hydroxy, oxo, ($C_1$–$C_6$)alkyl, ($C_1$–$C_6$) alkoxy, phenyl-($C_1$–$C_2$)alkyl or —$C(O)$—$Q^1$—$Q^2$—$Q^3$;

$R^3$ and $R^4$ are independently hydrogen; ($C_1$–$C_6$)alkyl optionally substituted independently with up to three halo, hydroxy, cyano or ($C_1$–$C_6$)alkoxy; $R^5$-carbonyl; or ($C_3$–$C_{10}$)cycloalkyl-($C_0$–$C_4$)alkylenyl optionally substituted independently with a hydroxy, ($C_1$–$C_6$) alkoxy, mercapto, ($C_1$–$C_6$)alkylthio, amino, N—($C_1$–$C_6$)alkylamino, di- N—($C_1$–$C_6$)alkylamino or ($C_1$–$C_6$)alkyl;

$R^5$ is hydrogen or ($C_1$–$C_6$)alkyl optionally substituted with hydroxy, ($C_1$–$C_4$)alkoxy, mercapto or ($C_1$–$C_6$) alkylthio;

n is 0 or 1;

A is independently hydrogen or —$C(O)$—$Q^1$—$Q^2$—$Q^3$;

$Q^1$ is independently —O—, —NH—, —$N(Q^2$—$Q^3)$— or

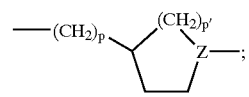

$Q^2$ is independently ($C_0$–$C_4$)alkylenyl or —$(CH_2CH_2$—$O)_r$;

$Q^3$ is independently hydrogen, hydroxy, methoxy, —O—$C(O)$—$X^1$, —$NHX^2$ or —$N(X^1)X^2$;

p and p' are independently , 0, 1, 2 or 3;

Z is independently —CH— or —N—;

r is independently 2, 3 or 4; and $X^1$ and $X^2$ are taken separately and are independently ($C_1$–$C_6$)alkyl; or $X^1$ and $X^2$ are taken together with the nitrogen atom to which they are attached to form a 3- to 10-membered azacycoalkyl.

13. A compound of the Formula IV

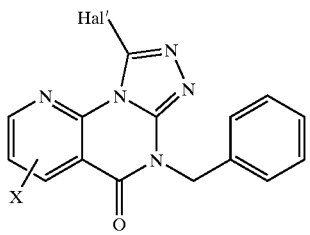

(IV)

or a pharmaceutically acceptable salt thereof, wherein:

X is hydrogen, hydroxy, halo, nitro, mercapto, cyano, carboxy, $(C_1-C_6)$alkyl, $(C_1-C_6)$alkoxy, $(C_1-C_6)$alkylthio, $(C_1-C_6)$alkylsulfinyl, $(C_1-C_6)$alkylsulfonyl, —NR$^3$R$^4$, —(N—A)$_n$—C(O)—Q$^1$—Q$^2$—Q$^3$ or a 3 to 10 membered azacycloalkyl; said alkyl, alkoxy, alkylthio, alkylsulfinyl and alkylsulfonyl in the definition of X being optionally substituted independently with up to three halo; said azacycloalkyl in the definition of X further optionally being bridged by $(C_1-C_6)$alkylenyl; said azacycloalkyl in the definition of X being optionally gem-dialkylated or independently substituted with up to three hydroxy, oxo, $(C_1-C_6)$alkyl, $(C_1-C_6)$alkoxy or —C(O)—Q$^1$—Q$^2$—Q$^3$;

R$^3$ and R$^4$ are independently hydrogen; $(C_1-C_6)$alkyl optionally substituted independently with up to three halo, hydroxy, cyano or $(C_1-C_6)$alkoxy; R$^5$-carbonyl; or $(C_3-C_{10})$cycloalkyl-$(C_0-C_4)$alkylenyl optionally substituted independently with a hydroxy, $(C_1-C_6)$alkoxy, mercapto, $(C_1-C_6)$alkylthio, amino, N—$(C_1-C_6)$alkylamino, di- N—$(C_1-C_6)$alkylamino or $(C_1-C_6)$alkyl;

R$^5$ is hydrogen or $(C_1-C_6)$alkyl optionally substituted with hydroxy, $(C_1-C_4)$alkoxy, mercapto or $(C_1-C_6)$alkylthio;

n is 0 or 1;

A is independently hydrogen or —C(O)—Q$^1$—Q$^2$—Q$^3$;

Q$^1$ is independently —O—, —NH—, —N(Q$^2$—Q$^3$)— or

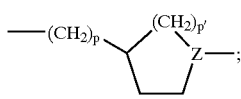

Q$^2$ is independently $(C_0-C_4)$alkylenyl or —(CH$_2$CH$_2$—O)$_r$;

Q$^3$ is independently hydrogen, hydroxy, methoxy, —O—C(O)—X$^1$, —NHX$^2$ or —N(X$^1$)X$^2$;

p and p' are independently , 0, 1, 2 or 3;

Z is independently —CH— or —N—;

r is independently 2, 3 or 4; and

X$^1$ and X$^2$ are taken separately and are independently $(C_1-C_6)$alkyl; or

X$^1$ and X$^2$ are taken together with the nitrogen atom to which they are attached to form a 3- to 10-membered azacycloalkyl.

14. A compound of the Formula V

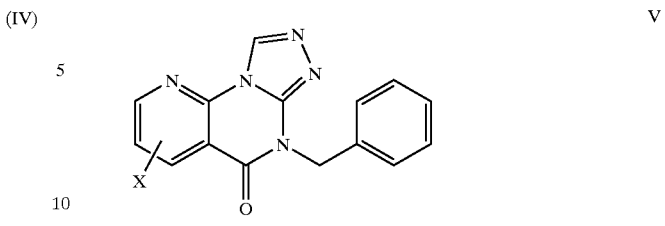

V or a pharmaceutically acceptable salt thereof, wherein:

X is hydrogen, hydroxy, halo, nitro, mercapto, cyano, carboxy, $(C_1-C_6)$alkyl, $(C_1-C_6)$alkoxy, $(C_1-C_6)$alkylthio, $(C_1-C_6)$alkylsulfinyl, $(C_1-C_6)$alkylsulfonyl, —NR$^3$R$^4$, —(N—A)$_n$—CO(O)—Q$^1$—Q$^2$—Q$^3$ or a 3 to 10 membered azacycloalkyl; said alkyl, alkoxy, alkylthio, alkylsulfinyl and alkylsulfonyl in the definition of X being optionally substituted independently with up to three halo; said azacycloalkyl in the definition of X further optionally being bridged by $(C_1-C_6)$alkylenyl; said azacycloalkyl in the definition of X being optionally gem-dialkylated or independently substituted with up to three hydroxy, oxo, $(C_1-C_6)$alkyl, $(C_1-C_6)$alkoxy or —C(O)—Q$^1$—Q$^2$—Q$^3$;

R$^3$ and R$^4$ are independently hydrogen; $(C_1-C_6)$alkyl optionally substituted independently with up to three halo, hydroxy, cyano or $(C_1-C_6)$alkoxy; R$^5$-carbonyl; or $(C_3-C_{10})$cycloalkyl-$(C_0-C_4)$alkylenyl optionally substituted independently with a hydroxy, $(C_1-C_6)$alkoxy, mercapto, $(C_1-C_6)$alkylthio, amino, N—$(C_1-C_6)$alkylamino, di- N—$(C_1-C_6)$alkylamino or $(C_1-C_6)$alkyl;

R$^6$ is hydrogen or $(C_1-C_6)$alkyl optionally substituted with hydroxy, $(C_1-C_4)$alkoxy, mercapto or $(C_1-C_6)$alkylthio;

n is 0 or 1;

A is independently hydroge or —C(O)—Q$^1$—Q$^2$—Q$^3$;

Q$^1$ is independently —O—, —N—, —N(Q$^2$—Q$^3$)— or

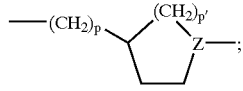

Q$^2$ is independently $(C_0-C_4)$alkylenyl or —(CH$_2$CH$_2$—O)$_r$;

Q$^3$ is independently hydrogen, hydroxy, methoxy, —O—C(O)—X$^1$, —NHX$^2$ —N(X$^1$)X$^2$;

p and p' are independently , 0, 1, 2 or 3;

Z is independently —CH— or —N—;

r is independently 2, 3 or 4; and

X$^1$ and X$^2$ are taken separately and are independently $(C_1-C_6)$alkyl; or

X$^1$ and X$^2$ are taken together with the nitrogen atom to which they are attached to form a 3- to 10-membered azacycloalkyl.

15. A method of treating an inflammatory condition involving the production of TNFα in a mammal comprising administering to said mammal a therapeutically effective amount of a compound of claim 1 or a pharmaceutically acceptable salt thereof.

16. A method of claim 15 wherein said inflammatory condition is chronic obstructive pulmonary disease or asthma.

17. A method of treating an inflammatory condition involving the production of TNFα in a mammal comprising administering to said mammal a therapeutically effective amount of a pharmaceutical composition of any one of claims 8–11.

18. A method of claim 17 wherein said inflammatory condition is chronic obstructive pulmonary disease or asthma.

* * * * *